US009580690B2

(12) United States Patent
Weaver et al.

(10) Patent No.: US 9,580,690 B2
(45) Date of Patent: *Feb. 28, 2017

(54) ATTENUATED RECOMBINANT ALPHAVIRUSES INCAPABLE OF REPLICATING IN MOSQUITOES AND USES THEREOF

(71) Applicant: The Board of Regents of the University of Texas System, Austin, TX (US)

(72) Inventors: Scott C. Weaver, Galveston, TX (US); Ilya V. Frolov, Birmingham, AL (US); Elena Frolova, Birmingham, AL (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 294 days.

This patent is subject to a terminal disclaimer.

(21) Appl. No.: 13/855,960

(22) Filed: Apr. 3, 2013

(65) Prior Publication Data

US 2014/0010841 A1     Jan. 9, 2014

Related U.S. Application Data

(60) Division of application No. 12/804,535, filed on Jul. 23, 2010, now Pat. No. 8,426,188, which is a continuation-in-part of application No. PCT/US2009/000458, filed on Jan. 23, 2009.

(60) Provisional application No. 61/062,228, filed on Jan. 24, 2008.

(51) Int. Cl.
     *C12N 7/00*          (2006.01)
     *A61K 39/12*       (2006.01)
     *C12N 15/86*      (2006.01)
     *A61K 39/00*       (2006.01)

(52) U.S. Cl.
     CPC ............... *C12N 7/00* (2013.01); *A61K 39/12* (2013.01); *C12N 15/86* (2013.01); *A61K 2039/5254* (2013.01); *C12N 2770/36134* (2013.01); *C12N 2770/36161* (2013.01); *C12N 2840/203* (2013.01)

(58) Field of Classification Search
None
See application file for complete search history.

(56) References Cited

U.S. PATENT DOCUMENTS

| 8,426,188 B2 | 4/2013 | Weaver et al. |
| 2003/0096397 A1 | 5/2003 | Schlesinger et al. |
| 2007/0166820 A1 | 7/2007 | Smith |

FOREIGN PATENT DOCUMENTS

| CA | 2327189 A1 | 6/2002 |
| WO | PCT/US2004/008458 A2 | 10/2004 |

OTHER PUBLICATIONS

Kim et al. Design of Chimeric Alphaviruses with a Programmed, Attenuated, Cell Type-Restricted Phenotype. Journal of Virology 85(9), 4363-4376 (2011).
Plante et al. Novel Chikungunya Vaccine Candidate with an IRES-Based Attenuation and Host Range Alteration Mechanism, Plos Pathogens 7(7), E1002142 (1-11) (2011).
Volkova et al. IRES-dependent replication of Venezuelan equine encephalitis virus makes it highly attenuated and incapable of replicationg in mosquito cells. Virology 377, 160-169 (2008).

*Primary Examiner* — Stacy B Chen
(74) *Attorney, Agent, or Firm* — Norton Rose Fulbright US LLP

(57) ABSTRACT

The present invention discloses an attenuated recombinant alphavirus that is incapable of replicating in mosquito cells and of transmission by mosquito vectors. These attenuated alphavirus may include but is not limited to Western Equine Encephalitis virus, Eastern equine encephalitis virus, Venezuelan equine encephalitis virus or Chikungunya virus. The present invention also discloses the method of generating such alphaviruses and their use as immunogenic compositions.

9 Claims, 13 Drawing Sheets

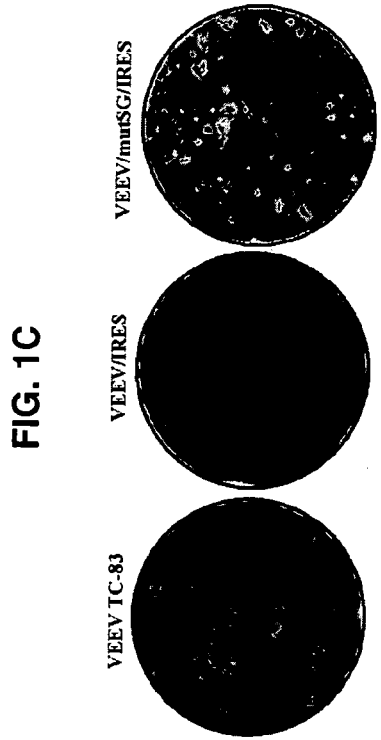
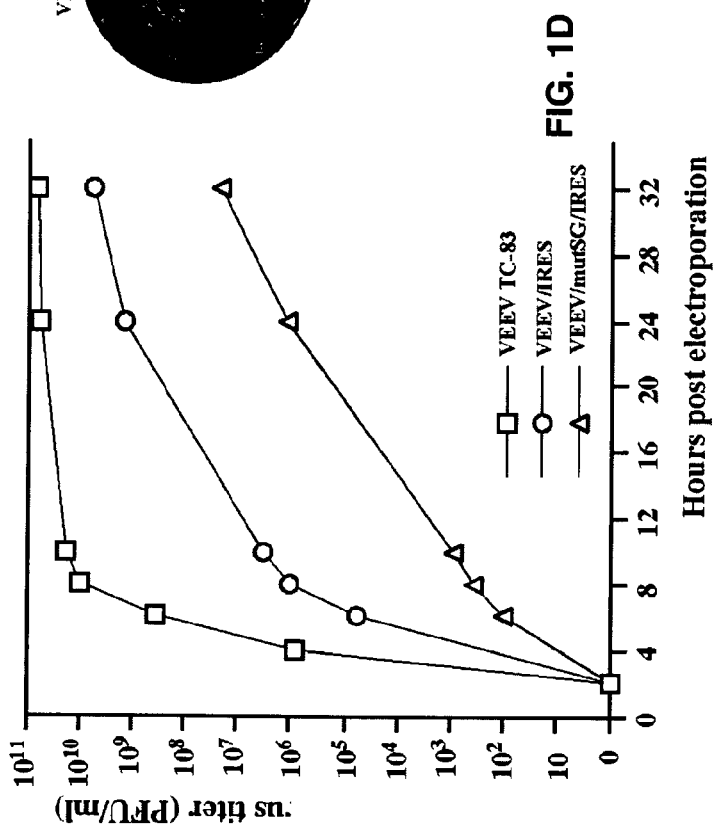
FIG. 1B
FIG. 1C
FIG. 1D

| Mutation | Isolate 1 | Isolate 2 | aa change |
|---|---|---|---|
| $A_{1613} \rightarrow G$ | + | + | Silent |
| $C_{1616} \rightarrow A$ | + | + | Silent |
| $T_{1619} \rightarrow C$ | + | + | Silent |
| $T_{2176} \rightarrow A$ | + | − | Silent |
| $A_{2758} \rightarrow G$ | + | + | $Y_{370} \rightarrow C$ |
| $A_{2760} \rightarrow C$ | + | − | $K_{371} \rightarrow Q$ |
| $T_{9702} \rightarrow C$ | + | + | Silent |
| $T_{10299} \rightarrow G$ | + | + | Silent |

VEEV/IRES genome

| nsP1 | nsP2 | nsP3 | nsP4 | ■ | C | E2 | E1 |

EMCV IRES

VEEV/mutSG/IRES genome

| nsP1 | nsP2 | nsP3 | nsP4 | ■ | C | E2 | E1 |

EMCV IRES

FIG. 5A

■ VEEV/IRES   □ VEEV/mutSG/IRES (bar chart, y-axis: $10$ to $10^{11}$; x-axis: P1, P2; n.d. at P2 for VEEV/mutSG/IRES)

FIG. 5B

SEQ ID NO. 4
ATGGACTACGACATAGTCTAGTCCGCCA----tatggccacaaccATG  pl. 1

SEQ ID NO. 5
ATGGACTACGACATAGTCTAGTCCGCCAAGtctatggccacaaccATG  pl. 2

SEQ ID NO. 6
ATGGACTACGACATAGTCTAGTCCGCCAAG---------------ATG  TC-83

ATTENUATED RECOMBINANT ALPHAVIRUSES INCAPABLE OF REPLICATING IN MOSQUITOES AND USES THEREOF

CROSS-REFERENCE TO RELATED APPLICATION

The present application is a divisional application of, and claims priority to, U.S. patent application Ser. No. 12/804,535, now U.S. Pat. No. 8,426,188, filed Jul. 23, 2010, which is a continuation-in-part application of, and claims benefit of priority under U.S.C. §120 of the international application PCT/US2009/000458, filed Jan. 23, 2009, which claims benefit of priority of provisional application U.S. Ser. No. 61/062,229 filed on Jan. 24, 2008. These applications are incorporated herein by reference in their entirety for all purposes.

FEDERAL FUNDING LEGEND

This invention was produced in part using funds obtained through a award 1U54 AI057156 from the National Institute of Health/National Institute of Allergy and Infectious Disease. Consequently, the federal government has certain rights in this invention.

BACKGROUND OF THE INVENTION

Field of the Invention

The present invention relates to the fields of molecular biology, virology and immunology of alphaviruses. More specifically, the present invention provides an attenuated, recombinant alphaviruses having mosquito infection incompetence and discloses a method of generating such alphaviruses and use of these attenuated alphaviruses in immunogenic compositions.

Description of the Related Art

The Alphavirus genus in the Togaviridae family contains a number of significant human and animal pathogens. These viruses are widely distributed on all continents except for the Antarctic region, and represent a significant public health threat (18, 39). Under natural conditions, most of the alphaviruses are transmitted by mosquitoes, in which they cause a persistent, life-long infection that has little effect on the biological functions of the vector. In vertebrates infected by mosquitoes during their blood meal, alphaviruses cause an acute infection, characterized by a viremia that is a prerequisite of infection of new mosquitoes and its circulation in nature.

Venezuelan equine encephalitis virus (VEEV) is one of the most pathogenic members of the alphavirus genus. It continuously circulates in South, Central and North America and causes sporadic epidemics and epizootics that involve humans, horses and other domestic animals. During the most recent major outbreak in Venezuela and Colombia (1995) involving subtype IC VEEV, about 100,000 human cases occurred, with over 300 fatal encephalitis cases estimated (37). During VEEV epizootics, equine mortality due to encephalitis can reach 83%, and while the overall mortality rate is low in humans (<1%), neurological disease, including disorientation, ataxia, mental depression, and convulsions, can be detected in up to 14% of infected individuals, especially children (21). The human disease caused by VEEV is characterized as a febrile illness with chills, severe headache, myalgia, somnolence and pharyngitis. Young and old individuals develop a reticuloendothelial infection with severe lymphoid depletion, followed by encephalitis. The result of the CNS infection is an acute meningoencephalitis that leads to the death of neuronal cells (9). The neurologic signs appear within 4-10 days of the onset of illness and include seizures, paresis, behavioral changes and coma.

In spite of the continuous threat of VEEV epidemics, no safe and efficient vaccines have been designed for this virus. The attenuated TC-83 strain of VEEV was developed more than four decades ago by serial passage of a highly virulent Trinidad donkey (TRD) strain of VEEV in guinea pig heart cells (4). Presently, TC-83 is still the only available vaccine for laboratory workers and military personnel. Over 8,000 people have been vaccinated (2, 8, 34), and the cumulative data unambiguously demonstrate that nearly 40% of all vaccines develop a disease with some symptoms typical of natural VEE, including fever, systemic illness and other adverse effects (2). This TC-83 strain universally kills newborn, but not adult, mice after i.c. and s.c. inoculation (31), and is thus a good starting material for further attenuation and study of the effects of the mutations on viral pathogenesis.

The VEEV genome is a nearly 12-kb-long, single-stranded RNA molecule of positive polarity that mimics the structure of cellular mRNAs. The genome RNA contains both a 5' methylguanylate cap and a 3' polyadenylate tail (24), features which allow translation of viral proteins by host cell machinery immediately after release of the genome RNAs from the nucleocapsids. The 5' two-thirds of the genome is translated into the nonstructural proteins (nsPs) that comprise the viral components of the replicative enzyme complex required for replication of the viral genome and transcription of the subgenomic RNA. The subgenomic RNA corresponds to the 3' third of the genome. It is synthesized from the subgenomic promoter and translated into the viral structural proteins. The attenuated phenotype of the VEEV strain TC-83 is the result of two mutations in the strain TRD genome: one of them replaced an amino acid at position 120 in E2 glycoprotein, and the second changed nt 3 in the 5'UTR (11, 23, 24, 43). Thus, because of the alphavirus' very high mutation rate, the reversion of TC-83 to a pathogenic phenotype remains a great concern in the event that the appropriate selective conditions, such as virus passage in vivo, would occur. Moreover, VEEV TC-83 is capable of replicating in mosquito cells, and infecting mosquitoes following vaccination (32); therefore, its transmission by mosquitoes remain possible.

Ideally, live arbovirus vaccine strains should not be transmissible by arthropod vectors, because circulation among reservoir hosts could lead to unforeseen changes that might include increased virulence. This is especially true for attenuated strains, produced from wild-type viruses that rely on small numbers of attenuating mutations that may be subject to reversion, or for genetically modified strains that might evolve in unanticipated ways if they underwent vector-borne circulation. The former risk was underscored by the detection of the VEEV TC-83 vaccine strain in mosquitoes collected in Louisiana during 1971 (32), an area outside the epizootic/epidemic that was restricted to Texas.

The development of infectious cDNA for alphaviruses opened an opportunity to explore their attenuation by extensively modifying the viral genomes, an approach that might minimize or exclude the reversion to the wt, pathogenic phenotype. Moreover, the genomes of such alphaviruses can be engineered to contain RNA elements that would be functional only in cells of vertebrate, but not insect, origin. Thus, such extensive mutations could prevent transmission of the genetically modified viruses by mosquito vectors.

Despite its importance as an emerging human and animal pathogen, its potential as a biological weapon and concerns about application of attenuated alphaviruses, the prior art is deficient in methods of generating attenuated strains of alphaviruses that are capable of replicating only in vertebrate cells. The present invention fulfills this long-standing need and desire in the art.

SUMMARY OF THE INVENTION

In one embodiment of the present invention, there is provided a method of generating an attenuated recombinant alphavirus. Such a method comprises cloning the internal ribosomal entry site of encephalomyelocarditis virus (EMCV IRES) between the end of non-structural protein 4 (nsP4) coding sequence and initiating AUG of a subgenomic RNA coding sequence of an alphavirus instead of natural 5' UTR of subgenomic RNA. The subgenomic promoter is inactivated with a large number of synonymous mutations such that the IRES must be retained to drive expression of the structural proteins. In a further related embodiment of the present invention, there is an attenuated recombinant alphavirus generated by the method discussed supra.

In another embodiment of the present invention, is provided a method of generating attenuated, recombinant alphavirus, comprising the steps of retaining the subgenomic promoter and positioning the capsid protein gene downstream of the envelope protein genes; and cloning internal ribosomal entry site of encephalomyelocarditis virus (EMCV IRES) between the end of the envelope protein genes and the capsid protein gene.

In another embodiment of the present invention, there is provided a method of generating attenuated, recombinant alphavirus, comprising the steps of: cloning an internal ribosomal entry site of a encephalomyelocarditis virus between the end of nonstructural protein 4 coding sequence and initiating AUG of a subgenomic RNA coding sequence of an alphavirus, instead of a natural 5' UTR of the subgenomic RNA; inactivating the subgenomic promoter of the alphavirus by clustered point mutations and deletion of the natural 5'UTR in the subgenomic RNA; positioning the capsid protein gene downstream of the inactivated subgenomic promoter under control of the internal ribosomal entry site of said encephalomyelocarditis virus; and positioning the envelope glycoprotein genes under a subgenomic promoter cloned downstream of the termination codon of the capsid gene, thereby generating the attenuated, recombinant alphavirus.

In yet another related embodiment of the present invention, there is provided a vector comprising a nucleotide sequence encoding the attenuated recombinant alphavirus and a host cell comprising and expressing this vector. In a yet another related embodiment of the present invention, there is provided a pharmaceutical composition. This composition comprises the attenuated recombinant alphavirus discussed supra and a pharmaceutically acceptable carrier. In a related embodiment of the present invention, there is provided an immunogenic composition. This immunogenic composition comprises the attenuated recombinant alphavirus described herein.

In another related embodiment of the present invention, there is provided a method of protecting a subject from infections resulting from exposure to an alphavirus. Such a method comprises administering an immunologically effective amount of the immunogenic composition comprising the attenuated, recombinant alphavirus described herein, thereby protecting the individual from the infections resulting from the exposure to the alphavirus.

BRIEF DESCRIPTION OF THE DRAWINGS

FIGS. 1A-1D show replication of the recombinant, EMCV IRES-encoding, VEEV TC-83-derived viruses in BHK-21 cells. FIG. 1A is a schematic representation of the designed viral genomes, infectivities of the in vitro-synthesized RNAs in the infectious center assay, virus titers at 24 h post transfection of 1 mg of the in vitro-synthesized RNAs into BHK-21 cells, and sizes of the plaques, formed by indicated viruses in BHK-21 cells at 48 h post transfection. Arrows indicate functional subgenomic promoters. Filled boxes indicate EMCV IRES. FIG. 1B shows alignment of the subgenomic promoter-containing fragment (SEQ ID NO: 1) of the VEEV TC-83 genome and the corresponding fragment of the VEEV/mutSG/IRES (SEQ ID NO: 2). The position of the promoter is indicated by open box. The start of the subgenomic RNA in the VEEV TC-83 genome and the beginning of the EMCV IRES are indicated by arrows. The mutations, introduced into the VEEV/mutSG/IRES genome are shown in lower case letters. FIG. 1C shows plaques, formed in BHK-21 cells by viruses, harvested at 24 h post transfection. FIG. 1D shows replication of the viruses after transfection of 1 mg of the in vitro-synthesized RNAs into BHK-21 cells.

FIGS. 2A-2C show mutations found in the plaque-purified VEEV/mutSG/IRES variants, which demonstrated more efficient replication in BHK-21 cells, and the effect of the defined adaptive mutations on VEEV TC-83 and VEEV/mutSG/IRES replication. FIG. 2A shows the list of the mutations, found in the genomes of plaque isolates, compared to the published sequence of VEEV TC-83 (24). FIG. 2B is a schematic representation of the VEEV TC-83 and VEEV/mutSG/IRES genomes, having either one or both identified mutations, and the infectivity of the in vitro-synthesized viral RNAs in the infectious center assay. Functional subgenomic promoters are indicated by arrows, and EMCV IRES by filled boxes. FIG. 2C shows replication of the designed viruses in BHK-21 cells after transfection of 1 mg of the in vitro-synthesized viral genomes.

FIG. 3A shows a list of the mutations identified in the genomes of the plaque-purified isolates from virus stock, harvested at 24 h post transfection of the in vitro-synthesized RNA (Orig.), and in the genomes of isolates from the stock that was additionally passaged three times in Vero cells (Pass.). FIG. 3B shows localization of the defined mutations in the VEEV nsP2. The positions of currently known functional domains in alphavirus nsP2 (38, 39) are indicated.

FIGS. 4A-4B show an analysis of protein and RNA synthesis in BHK-21 cells transfected with the in vitro-synthesized recombinant viral RNAs. Cells were electroporated with 4 mg of the indicated RNAs and seeded into 35-mm dishes. In FIG. 4A, at 4.5 h post transfection, medium in the wells was replaced by 1 ml of aMEM supplemented with 10% FBS, ActD (1 mg/ml) and [$^3$H] uridine (20 mCi/ml). After 4 h of incubation at 37° C., RNAs were isolated and analyzed by agarose gel electrophoresis. The positions of viral genomic and subgenomic RNAs are indicated by G and SG, respectively. The VEEV/IRES-specific subgenomic RNA forms a more diffuse band than do other, subgenomic RNA-producing, viruses, because, in the gel, it co-migrates with the ribosomal 28S RNA. In FIG. 4B, at 12 h post transfection, protein were metabolically labeled with [$^{35}$S]methionine and analyzed on a sodium dodecyl sulfate-10% polyacrylamide gel. The positions of molecular weight markers (kDa) are indicated at the left side of the gel. The positions of viral structural proteins: C, E1 and p62 (the precursor of E2) are shown at the right side of the gel. Asterisks indicate the positions of cellular proteins (the heat-shock proteins), induced by replication of the IRES-encoding viruses.

FIGS. 5A-5C show passaging of the recombinant, EMCV IRES-containing VEEV variants in $C_7 10$ cells. FIG. 5A is a schematic representation of viral genomes. Arrow indicates the position of the functional subgenomic promoter. The filled box indicates the position of EMCV IRES. FIG. 5B shows titers of the recombinant viruses after passaging in $C_7 10$ cells. Cells in 35-mm dishes were infected with 400 ml of virus samples harvested either at 24 h post transfection of BHK-21 cells with the in vitro-synthesized RNA (P1) or 48 h post infection of $C_7 10$ cells. Dashed line indicates the limit of detection. FIG. 5C shows the deletions of the IRES-containing sequence (SEQ ID NOS: 4-5) identified in the plaque-purified VEEV/IRES variants, demonstrating efficient replication in $C_7 10$ cells. The residual EMCV IRES-specific sequences are indicated by lower case letters. The VEEV/IRES variants are aligned with TC-83 strain of VEEV (SEQ ID NO: 6).

FIG. 6 shows replication of VEEV/mutSG/IRES/1 and VEEV TC-83 in the NIH 3T3 cells. Cells were infected at an MOI of 10 PFU/cell. Media were replaced at the indicated time points, and virus titers were measured by plaque assay on BHK-21 cells. The same samples were used to measure IFN-a/b release in biological assay. Concentrations of released IFN-a/b are presented in international units (IU) per ml.

FIG. 7 shows survival of mice infected with VEEV TC-83 and VEEV/mutSG/IRES/1 viruses. Six-day-old NIH Swiss mice were inoculated i.c. with ca. $10^6$ PFU of the indicated viruses. Animals were monitored for two months. No deaths occurred after day 9 post-infection in any of these experiments.

FIG. 8 shows survival following vaccination and challenge of adult mice. Five-to-6-week-old female NIH Swiss mice were immunized s.c. with VEEV strain TC-83 or the recombinant virus at a dose of ca. $10^6$ PFU. Three weeks after immunization, mice were challenged s.c. with ca. $10^4$ PFU of VEEV strain 3908, and mortality was recorded.

FIG. 10 is a schematic representation showing genetic strategy for chikungunya virus (CHIKV) CHIK/IRES constructs.

FIG. 11 shows Viremia titers in 6-day-old CD1 mice after subcutaneous infection with CHIKV strains ($10^6$ PFU). Dashed line is the limit of detection in the plaque assays.

FIG. 12 shows Virus titers in the legs of 6-day-old CD1 mice after subcutaneous infection with CHIKV strains ($10^6$ PFU).

FIG. 14 depicts survival of adult CD1 mice 4 weeks after vaccination with 105 PFU and intranasal challenge with the Ross strain of CHIKV.

DETAILED DESCRIPTION OF THE INVENTION

Figure 1A:
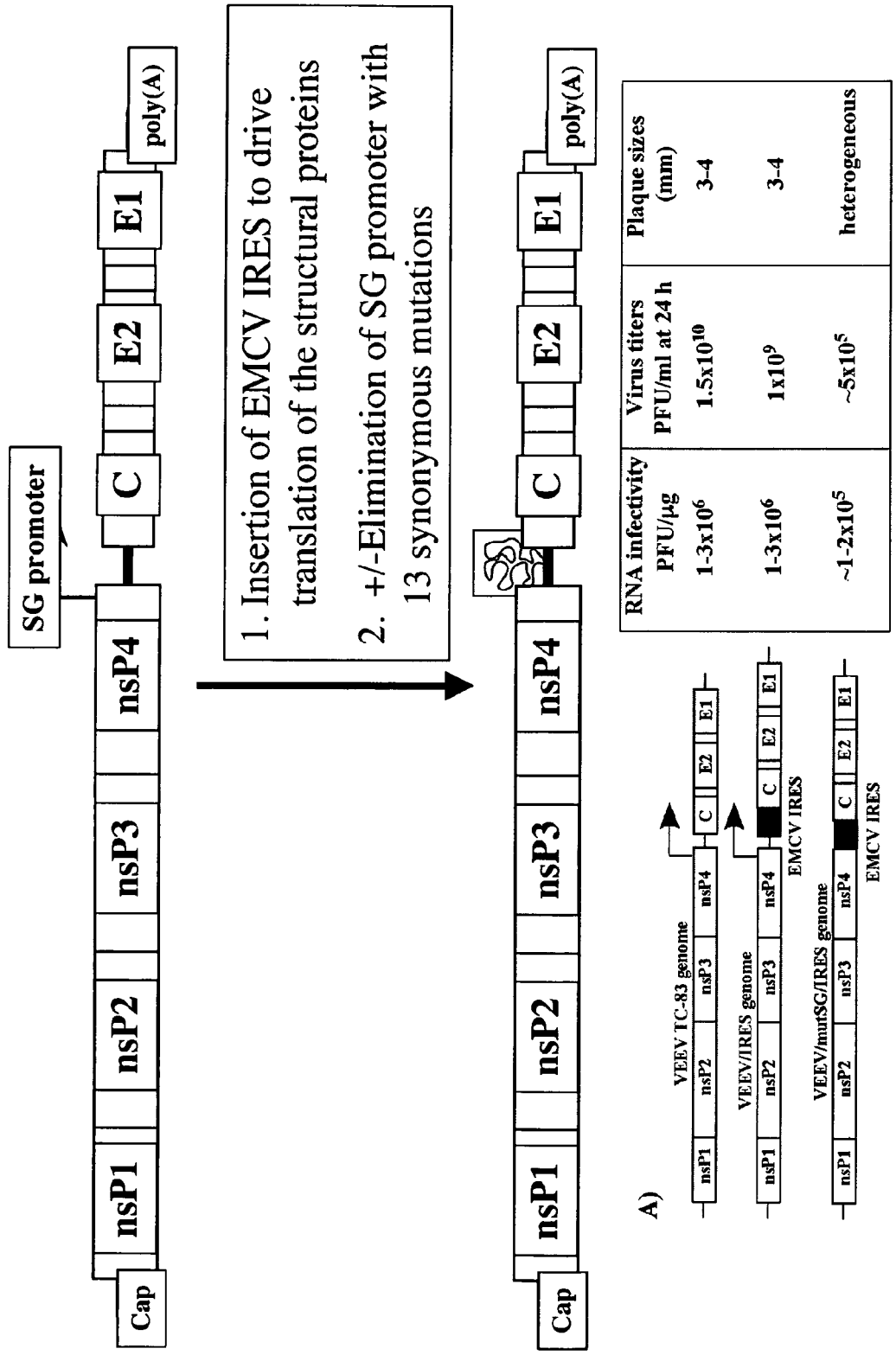

The present invention is drawn to a new strategy of developing attenuated strains of alphaviruses. These attenuated alphaviruses are capable of replicating efficiently only in vertebrate cells. This phenotype was achieved by rendering the translation of the viral structural proteins and ultimately, viral replication dependent on the internal ribosome entry site of encephalomyocarditis virus (EMCV IRES). Such a recombinant virus is viable and demonstrated highly attenuated phenotype in newborn mice, yet induces protective immunity against VEEV infection and CHIKV. Further, formalin-inactivated vaccines are expensive and inefficient. In addition to this, these vaccines also require multiple, repeated vaccinations. Furthermore, the only available live attenuated vaccine against VEEV infection is very reactogenic and infects mosquitoes during the blood meal on vaccinated horses. The attenuated alphaviruses discussed herein provide a significant advantage over the vaccines that are currently available since the attenuated phenotype is irreversible. Further, the genetically engineered alphaviruses are not able to replicate in mosquito cells, thus, suggesting a new approach for generating new, live recombinant viruses, which are not capable of replicating in mosquitoes and thus, incapable of circulating in nature.

The development of the infectious cDNA clones of Sindbis and other alphaviruses (12, 25, 36) opened the opportunity not only for the reverse genetics experiments aimed at studying different aspects of the virus biology and pathogenesis, but also for the development of new recombinant vaccines. Attenuation of the viruses by passaging either in tissue culture or in chicken embryos (29) generally results from accumulation of small numbers of point mutations in the structural and nonstructural genes, and in the cis-acting elements of viral genomes. For example, the VEEV TC-83 vaccine strain relies on only 2 point mutations for its attenuation, and the high degree of reactogenicity (34) probably reflects the instability of this attenuation mechanism. This raises a concern about the possible reversion to the wt, pathogenic phenotype during virus replication in vaccinated individuals. The number of mutations can be additionally increased by chemical mutagenesis (28), but this procedure also does not make the introduced changes irreversible. The genetic manipulations with infectious cDNA clones of the RNA$^+$ viruses open great possibilities for stronger modification of viral genomes, and provide an opportunity to introduce, extensive deletions that would make it impossible to revert to the wt genome sequence (5, 6, 10, 19), or additional genetic material that might enhance the immunogenicity of the variants.

There is also a great concern that genetically altered arboviruses might be introduced into the natural circulation, mediated by mosquito vectors, and demonstrate a further evolution during long-term replication, either in mosquitoes or during viremia development in vertebrate hosts. An example is the use of VEEV TC-83, which is capable of producing levels of viremia in equids sufficient for infecting mosquitoes. The isolation of TC-83 from naturally infected mosquitoes collected in Louisiana (32) during the 1971 Texas epidemic underscored the risk of transmission of the attenuated alphaviruses. Therefore, in designing a new generation of live vaccine strains, it is prudent to make arboviruses not only highly attenuated, but also capable of replicating only in cells of vertebrate origin. This can be achieved by cloning cell-specific RNA elements into viral genomes. In contrast to the cricket paralysis virus IRES (20), the EMCV-specific element was expected to function very inefficiently in arthropod cells.

In the present invention, the EMCV IRES was cloned into VEEV TC-83 genome and the chikungunya virus genome to make the translation of viral structural genes IRES-dependent. One of the genomes contained a functional subgenomic promoter, and the IRES in the 5'UTR of the subgenomic RNA. This virus was viable, but its ability to produce the subgenomic RNA promoted further evolution, which resulted in IRES deletion and reversion, most likely, to a standard, cap-dependent translation of the structural proteins. The latter deletions made it capable of replicating in mosquito cells. The second variant with multiple mutations to inactivate the subgenomic promoter was stable in terms of its inability to revert to a cap-dependent translation. Because such reversion would not only require the IRES deletion, but also the restoration of the subgenomic promoter, which was inactivated by 13 mutations, direct reversion of these multiple mutations probably represents a negligible risk. However, this variant of TC-83 developed an interesting way to evolve to a more efficiently replicating phenotype by accumulating additional, adaptive mutations in the nsP2 gene. These mutations did not noticeably change the level of viral RNA replication, synthesis of the viral structural proteins, or their compartmentalization in the cells. The detected mutations also did not create an additional signal that could increase the efficiency of the genome packaging. Thus, the mechanism of their functioning remains to be determined. However, the accumulating published data suggest that the packaging of the genomes of the RNA$^+$ viruses is strongly determined by the replicative complexes, and the genomes need to be presented by the functional nsPs to the structural proteins for particle formation (22, 30). The working hypothesis herein is that the helicase domain of the nsP2 might be involved in the viral genome's presentation for its packaging into the nucleocapsids, and, thus, the identified mutations could have a positive effect on the efficiency of this process.

The present invention sought to develop VEEV and CHIKV variants that are incapable of replicating in arthropod vectors and demonstrate a stable, more attenuated phenotype. Slower growth of the designed VEEV/mutSG/IRES/1 variant in both IFN-alpha/beta-competent and IFN signaling-deficient BHK-21 cells, its ability to induce higher levels of IFN-alpha/beta in tissue culture, its greatly reduced ability to kill newborn mice even after i.c. inoculation, and its inability to replicate in mosquito cells suggest that this variant might meet those requirements. Its immunogenicity will be further investigated in different animal models. Moreover, it is believed that other encephalogenic alphaviruses can be attenuated by using a similar, EMCV IRES-based strategy, which can be applied in combination with other approaches that have been developed within the recent years (1, 13-15, 31).

In summary, the present invention describes the development of attenuated alphaviruses and their application as a new type of vaccine against the encephalitogenic alphaviruses that include VEEV, EEEV and WEEV and other alphaviruses such as Chikungunya virus that cause disease in humans and livestock. Replication of such alphaviruses would depend on EMCV IRES, that makes them incapable of replicating in mosquito cells or mosquito vectors. More importantly, this phenotype is irreversible because of the extensive modifications introduced into viral genome. Therefore, these new variants can be used for vaccination without a concern about possibility of their transmission by natural mosquito vectors.

The present invention is directed to generating attenuated, recombinant alphavirus, comprising the step of: cloning the internal ribosomal entry site of encephalomyelocarditis virus (EMCV IRES) between the end of nonstructural protein (nsP4) coding sequence and initiating AUG of a subgenomic RNA coding sequence of an alphavirus instead of natural 5' UTR. This method may further comprise inactivating the subgenomic promoter of the alphavirus by clustered point mutations and deletion of the natural 5' UTR in the subgenomic RNA. Further, the inactivation of the subgenomic promoter may not modify the carboxy terminus of non-structural protein 4. Additionally, the method may further comprise introducing adaptive mutations in non-structural protein 2 (nsP2) effective to increase virus replication, release and virus titers. Examples of the adaptive mutations in non-structural protein 2 may include but are not limited to $Y_{370} \rightarrow C$, $K_{371} \rightarrow Q$, $P_{349} \rightarrow T$, $D_{418} \rightarrow A$, $K_{423} \rightarrow T$ or combinations thereof. Furthermore, examples of the alphavirus may include but is not limited to Venezuelan Equine Encephalitis virus (VEEV), Eastern Equine Encephalitis Virus (EEEV), Western Equine Encephalitis virus (WEEV) or Chikungunya virus.

In an embodiment of the present invention, there is provided a method of generating attenuated, recombinant alphavirus, comprising the steps of positioning the capsid protein gene downstream of the envelope protein genes; and cloning internal ribosomal entry site of encephalomyelocarditis virus (EMCV IRES) between the end of the envelope protein genes and the capsid protein gene.

In another embodiment of the present invention, there is provided a method of generating attenuated, recombinant alphavirus, comprising the steps of: cloning an internal ribosomal entry site of a encephalomyelocarditis virus between the end of nonstructural protein 4 coding sequence and initiating AUG of a subgenomic RNA coding sequence of an alphavirus, instead of a natural 5' UTR of the subgenomic RNA; inactivating the subgenomic promoter of the alphavirus by clustered point mutations and deletion of the natural 5'UTR in the subgenomic RNA; positioning the capsid protein gene downstream of the inactivated subgenomic promoter under control of internal ribosomal entry site of said encephalomyelocarditis virus; and positioning envelope glycoprotein genes under a subgenomic promoter cloned downstream of the termination codon of capsid gene, thereby generating the attenuated, recombinant alphavirus.

The present invention is also directed to an attenuated recombinant alphavirus generated by one of the methods described herein. Such an alphavirus may be incapable of replicating in mosquitoes, incapable of transmission by mosquito vectors, capable of inducing high levels of IFN alpha/beta, slow growth in IFN alpha/beta cells, slow growth in IFN signaling-deficient BHK-21 cells or a combination thereof.

The present invention is still further directed to a vector comprising a nucleotide sequence encoding the attenuated recombinant alphavirus generated by one of the methods described herein and a host cell comprising and expressing the vector. Constructing vectors and expressing them in cells is well-known and standardized technique in the art. Hence, one of skill in the art may construct such vectors based on routine experimentation and knowledge that is available in the art.

The present invention is further directed to a pharmaceutical composition, comprising the attenuated recombinant alphavirus discussed supra and a pharmaceutically acceptable carrier. The present invention is also directed to an immunogenic composition, comprising an attenuated recombinant alphavirus generated by one of the methods described herein.

The present invention is still further directed to a method of protecting a subject from infections resulting from exposure to an alphavirus, comprising the step of: administering immunologically effective amount of the immunogenic composition discussed supra, thereby protecting the subject from infections resulting from exposure to the alphavirus. The subject benefiting from such a method may be human or livestock.

The present invention is still further directed to a method of generating attenuated, recombinant alphavirus incapable of infecting mosquitoes, comprising the step of cloning the internal ribosomal entry site of encephalomyelocarditis virus and capsid genes downstream of the envelope glycoprotein genes with said capsid gene at the 3' end of the subgenomic region just upstream of the 3' UTR, wherein the capsid is expressed in a cap-independent manner and the envelope protein genes is translated in a cap-dependent manner but the capsid protein translated in an IRES-dependent manner.

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof.

The composition described herein can be administered independently, either systemically or locally, by any method standard in the art, for example, subcutaneously, intravenously, parenterally, intraperitoneally, intradermally, intramuscularly, topically, or nasally. Dosage formulations of the composition described herein may comprise conventional non-toxic, physiologically or pharmaceutically acceptable carriers or vehicles suitable for the method of administration and are well known to an individual having ordinary skill in this art.

The composition described herein may be administered independently one or more times to achieve, maintain or improve upon a therapeutic effect. It is well within the skill of an artisan to determine dosage or whether a suitable dosage of the composition comprises a single administered dose or multiple administered doses. An appropriate dosage depends on the subject's health, the induction of immune response and/or prevention of infection caused by the alphavirus, the route of administration and the formulation used.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

Example 1

Cell Cultures

The BHK-21 cells were provided by Paul Olivo (Washington University, St. Louis, Mo.), and the Vero cells by Charles Rice (Rockefeller University, NY, N.Y.). The NIH 3T3 cells were obtained from the American Type Tissue Culture Collection (Manassas, Va.). These cell lines were maintained at 37° C. in alpha minimum essential medium (aMEM) supplemented with 10% fetal bovine serum (FBS) and vitamins. Mosquito $C_7 10$ cells were obtained from Henry Huang (Washington Univ., St. Louis, Mo.) and propagated in DMEM supplemented with 10% heat-inactivated FBS and 10% tryptose phosphate broth (TPB).

Example 2

Plasmid Constructs

Standard recombinant DNA techniques were used for all plasmid constructions. The original plasmid with VEEV TC-83 genome under the control of SP6 RNA polymerase promoter, pVEEV TC-83, was described (33). pVEEV/IRES contained EMCV IRES with the first 4 codons of the EMCV polyprotein. This sequence was cloned into the VEEV subgenomic RNA-coding sequence between the end of the 5'UTR and the initiating AUG. pVEEV/mutSG/IRES encoded the VEEV TC-83 genome, in which the subgenomic promoter was inactivated by clustered point mutations, which did not modify the amino acid sequence (SEQ ID NO: 3) of the carboxy terminus of nsP4 (FIGS. 1A and 1B). This viral genome had the 5'UTR of the subgenomic RNA deleted. Thus, VEEV TC-83 nonstructural and structural proteins were expected to be synthesized from the same genomic RNA. The adaptive mutations were introduced into pVEEV/mutSG/IRES-encoded nsP2 by PCR amplification of the fragments of interest of the selected variants, followed by replacement of the corresponding fragment in the original genome. The same PCR-based technique was used for synthesis cloning of different fragments into the SphI site in the 3'UTR of the VEEV/mutSG/IRES genome. All of the cloned fragments were sequenced before further experiments with the rescued viruses.

Example 3

RNA Transcriptions

Plasmids were purified by centrifugation in CsCl gradients and linearized by MluI digestion. RNAs were synthesized by SP6 RNA polymerase (Ambion) in the presence of cap analog (New England Biolabs). The yield and integrity of transcripts were analyzed by gel electrophoresis under non-denaturing conditions. RNA concentration was measured on a Fluor Chem imager (Alpha Innotech), and transcription reactions were used for electroporation without additional purification.

Example 4

RNA Transfections

Electroporation of BHK-21 cells was performed under described conditions (27). To rescue the viruses, 1 mg of in vitro-synthesized viral genome RNA was electroporated into the cells (27), and then they were seeded into 100-mm dishes and incubated until cytopathic effects were observed. Virus titers were determined using a standard plaque assay on BHK-21 cells (26).

To assess the RNA infectivity, 10-fold dilutions of electroporated BHK-21 cells were seeded in 6-well Costar plates containing subconfluent, naïve cells. After a 1 h incubation at 37° C. in a 5% $CO_2$ incubator, cells were overlaid with 2 ml of MEM-containing 0.5% Ultra-Pure agarose supplemented with 3% FBS. Plaques were stained with crystal violet after 2 days incubation at 37° C., and infectivity was determined in plaque-forming units (PFU) per mg of transfected RNA.

Example 5

Sequencing of Viral Genomes

Large plaques were randomly selected during titering of viral stocks (without staining with neutral red). Viruses were extracted from the agarose plugs into MEM, and aliquots of the latter media were used to infect BHK-21 cells in 35-mm dishes. After development of profound CPE, virus stocks were harvested for further characterization, and RNAs were isolated from the infected cells by TRizol reagent according to the instructions of the manufacturer (Invitrogen). ~1000 nt-long, overlapping fragments were synthesized using standard RT-PCR techniques, purified by agarose gel electrophoresis and sequenced. Sequencing of the 5'UTR was performed by using a FirstChoice RLM-RACE Kit (Ambion) as described (16).

Example 6

Viral Replication Analysis

One-fifth of the electroporated cells were seeded into 35-mm dishes. At the times indicated in the figures, media were replaced and virus titers were determined by plaque assay on BHK-21 cells (26). Alternatively, BHK-21, NIH3T3 or $C_7 10$ cells were seeded into 35-mm dishes and infected at the MOIs indicated in the figures. Media were replaced by fresh media, and virus titers in the harvested samples were determined by plaque assay on BHK-21 cells.

Example 7

Analysis of Protein Synthesis

BHK-21 cells were electroporated with 4 mg of the indicated RNAs, and one-fifth of the electroporated cells were seeded into six-well Costar plates. At 12 h post transfection, proteins were metabolically labeled by incubating for 30 min in 0.8 ml of DMEM medium lacking methionine, supplemented with 0.1% FBS and 20 mCi/ml of [$^{35}$S]methionine. After this incubation, they were scraped into the media, pelleted by centrifugation and dissolved in 100 μl of standard protein loading buffer. Equal amounts of proteins were loaded onto sodium dodecyl sulfate (SDS)-10% polyacrylamide gels. After electrophoresis, gels were dried and autoradiographed.

Example 8

RNA Analysis

To analyze the synthesis of virus-specific RNAs, cells were electroporated with 4 mg of the in vitro-synthesized viral RNAs, and one-fifth of the cells were seeded into 35-mm dishes as. At 4.5 h post transfection, medium in the wells was replaced by 1 ml of aMEM supplemented with 10% FBS, ActD (1 μg/ml) and [$^3$H]uridine (20 mCi/ml). After 4 h of incubation at 37° C., total cellular RNAs were isolated by Trizol (Invitrogen) according the Manufacturer's protocol, then denatured with glyoxal in dimethyl sulfoxide and analyzed by agarose gel electrophoresis using described conditions (7). Gels were impregnated with 2,5-diphenyloxazole (PPO), dried and autoradiographed.

Example 9

IFN-a/b Assay

The concentrations of IFN-a/b in the media were measured by a described biological assay (41). Briefly, L929 cells were seeded in 100 ml of complete media at a concentration of $5 \times 10^4$ cells/well in 96-well plates and incubated at 37° C. for 6 h. Samples of media harvested from infected NIH 3T3 cells were treated with UV light for 1 h, and serially diluted in two-fold steps directly in the wells with L929 cells. After incubation for 24 h at 37° C., an additional 100 ml of media with $2 \times 10^5$ PFU of vesicular stomatitis virus (VSV) was added to the wells and incubation continued for 36-40 h. Then cells were stained with crystal violet, and the end point was determined as the concentration of IFNa/b required to protect 50% of the cells from the VSV-induced CPE. The IFN-a/b standard for normalization of the results was purchased from the ATCC, and titers of the released viruses were determined by plaque assay on BHK-21 cells.

Example 10

Evaluation of Virus Replication in Mosquitoes

To assess replication competence in mosquitoes in vivo, intrathoracic inoculations of *Aedes aegypti* (a colony originating in Galveston, Tex.) mosquitoes using ca. $10^5$ PFU in a 1 μL volume were used. Intrathoracic inoculation was selected over oral exposure because nearly any culicine mosquito is highly susceptible to intrathoracic infection by any alphavirus, while oral susceptibility is highly variable and much less sensitive (42). Following inoculation using a glass pipette, mosquitoes were incubated 10 days at 27° C. and then titrated individually in 1 mL of MEM supplemented with 20% FBS and Fungizone. A 100 μL volume of each titrated mosquito was then added to a Vero cell monolayer on a 24 well plate and observed for 5 days for cytopathic effects to detect infection. Assay controls included both the TC-83 parent virus and the IRES mutant.

Example 11

Immunization and Challenge with Virulent VEEV

Six-day-old NIH Swiss mice were inoculated intracerebrally (i.c.) with VEEV TC-83 strain or the designed mutants at a dose of ca. $10^6$ PFU in a total volume of 20 μl of PBS. After infection, each cohort of 8-10 animals was maintained for 2 months without any manipulation. For 21 days, mice were observed daily for signs of illness (ruffled fur, depression, anorexia and/or paralysis) and/or death.

Eight-week-old female NIH Swiss mice were vaccinated s.c. at a dose of ca. $10^6$ PFU/mouse using VEEV TC-83 or the recombinant virus, then challenged subcutaneously 4 weeks later with ca. $10^4$ PFU of highly virulent VEEV strain 3908. For 21 days, mice were observed twice daily for signs of illness (ruffled fur, depression, anorexia and/or paralysis) and/or death.

Example 12

Recombinant VEEV TC-83-Based Viruses

The present invention developed alphaviruses capable of efficient replication in the cells of vertebrate, but not of mosquito origin. Therefore, replication of such viruses had to depend on proteins or RNA sequences that function only in vertebrate, but not in insect cells. To achieve this, the present invention designed a method to make expression of alphavirus structural proteins dependent on the EMCV IRES. The designed IRES did not contain the poly(C) sequence but retained the first 4 codons of EMCV polyprotein to achieve the most efficient translation of VEEV TC-83 structural genes. In later experiments, it was confirmed that these additional amino acids had no negative effect on virus replication, but had detectable positive effect on the translation of viral structural proteins.

In one of the constructs, VEEV/IRES, the IRES sequence was cloned into the subgenomic RNA downstream of the intact 5'UTR (FIG. 1A). Therefore, this genome was expected to be capable of subgenomic RNA synthesis. In another recombinant, VEEV/mutSG/IRES, the subgenomic promoter was inactivated by 13 synonymous point mutations (FIGS. 1A and 1B), which were expected to prevent reversion to an active SG RNA promoter. To promote synthesis of the VEEV structural proteins, the IRES sequence was cloned to replace the 26S 5'UTR.

The genome RNAs of VEEV/IRES, VEEV/mutSG/IRES and unmodified, wt VEEV TC-83 were synthesized in vitro and transfected into BHK-21 cells. In the infectious center assay, the VEEV/IRES RNA demonstrated the same infectivity as the RNA of TC-83, and developed plaques of a uniform size similar to those of the TC-83 (FIGS. 1A and 1C). This was a strong indication that no additional, adaptive mutations were required for productive replication of the designed virus. VEEV/IRES replicated to titers exceeding $10^9$ PFU/ml, but these final titers and virus replication rates were significantly slower (FIG. 1D) than those of VEEV TC-83. BHK-21 cells transfected with another recombinant viral genome, VEEV/mutSG/IRES, which lacked the subgenomic promoter, produced infectious virus very inefficiently (FIG. 1D). In the infectious center assay, this construct developed mainly pinpoint plaques, and their number was difficult to estimate. Surprisingly, this virus demonstrated further evolution upon serial passage and rapidly developed variants that produced larger plaques (FIG. 1C and data not shown). The growth curve presented in FIG. 1D represents the release of both small and large plaque-forming viruses.

Thus, the results of these experiments indicated that, at least in the context of the VEEV/IRES genome, EMCV IRES could produce structural proteins at levels sufficient for VEEV replication. The construct with a mutated subgenomic promoter, VEEV/mutSG/IRES, produced a defective-in-replication virus that could evolve for more efficient replication.

Example 13

Analysis of Adaptive Mutations in VEEV/mutSG/IRES

The evolution of VEEV/mutSG/IRES to a large plaque phenotype suggested an accumulation of additional mutations in the viral genome. The reversion to the wt genome sequence was an impossible event due to the large number of introduced point mutations, so the location of adaptive mutations was difficult to predict. To identify the mutations, 5 plaques of VEEV/mutSG/IRES samples harvested at 24 h post electroporation were randomly selected, and the entire genomes (including the 3' and 5'UTRs) of two plaque-purified variants were sequenced. The list of the mutations identified is presented in FIG. 2A. The majority of them were synonymous and were not present in the known cis-acting RNA elements. Thus, their effect on virus replication was very unlikely. However, the genomes of both plaque isolates contained the same mutation in the nsP2 protein, $Y_{370} \rightarrow C$, and one of the genomes had the next encoded aa changed as well ($K_{371} \rightarrow Q$).

To test the effect of the mutations on virus replication, $Y_{370} \rightarrow C$ and both $Y_{370} \rightarrow C$ and $K_{371} \rightarrow Q$ were cloned into the original VEEV/mutSG/IRES construct (FIG. 2B) and compared the RNA infectivity, virus replication rates and plaque sizes with those of the original VEEV/mutSG/IRES and other constructs. The same mutations were also cloned into the VEEV TC-83 genome to test their effect on the replication of this parental virus. The IRES-encoding genome RNAs with either one or both mutations in the genome, VEEV/mutSG/IRES/1 and VEEV/mutSG/IRES/2, demonstrated the same infectivity in the infectious center assay as did VEEV TC-83 RNA and rescued viruses formed uniform plaque sizes similar to those of the VEEV TC-83. They also demonstrated a strong increase in the growth rates (FIGS. 2C and 1D), but the effect of the second mutation was barely detectable. Thus, taken together, the data indicated that the $Y_{370} \rightarrow C$ mutation in the nsP2 had a strong positive effect on virus replication, and the second mutation did not noticeably improve it. When introduced into the VEEV TC-83 genome, the same mutations did not have any detectable effect on the rates of virus replication or on final titers (FIG. 2C), suggesting that the replication enhancement was specific to the VEEV/mutSG/IRES variant.

Figures 3A, 3B:
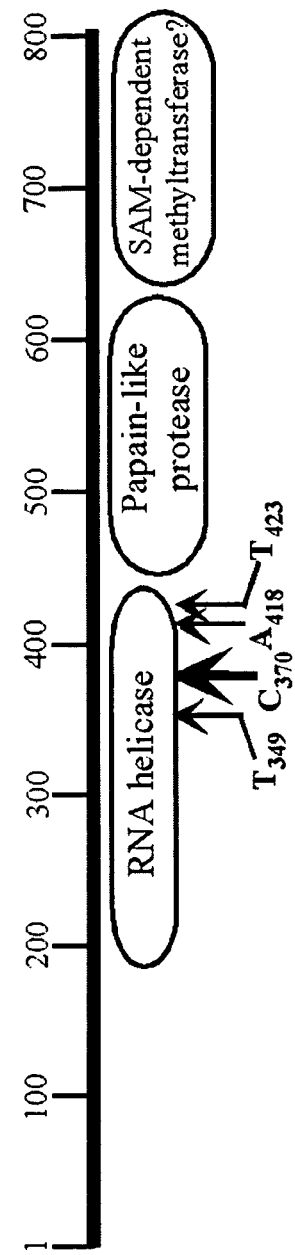
FIGS. 3A-3B shows mutations identified in the nsP2 protein of VEEV/mutSG/IRES variants demonstrating a large-plaque phenotype.

The identified aa changes ($Y_{370} \rightarrow C$ and $K_{371} \rightarrow Q$) could represent only a fraction of possible mutations leading to the efficient replication of the subgenomic promoter-deficient, IRES-containing virus. Therefore, in parallel experiments, nt 2161-2959 in the other three plaque clones isolated from the samples were sequenced, harvested at 24 h post RNA transfection of the in vitro-synthesized RNAs, and of 5 plaque-purified variants isolated from the virus stock after an additional 3 passages in Vero cells. It was anticipated that such passaging would lead to the selection of the most efficiently replicating viruses. The list of the identified mutations is presented in FIG. 3A. Sequencing was performed directly from the RT-PCR-derived DNA fragments; therefore, the presented mutations represent the consensus sequences in the plaque-derived virus population and are not PCR-derived (FIG. 3B).

All of the isolates contained mutations in the sequenced fragment, corresponding to the carboxy terminal fragment of the RNA helicase domain of nsP2, and all of the altered amino acids were located between amino acids 348-424. Moreover, the most common mutation, both in the original viral stock, generated after electroporation, and in the passaged pool, was $Y_{370} \rightarrow C$. This was an indication that it likely has one of the most prominent effects on replication; therefore, the above-described variant with this particular mutation, VEEV/mutSG/IRES/1, was used in the experiments outlined in the following sections.

Example 14

Effect of the nsP2 $Y_{370} \rightarrow C$ Mutation on Virus Replication

Identification of the adaptive mutation in the carboxy terminal fragment of the nsP2-associated RNA helicase was surprising and did not suggest any obvious explanation for the increase in VEEV/mutSG/IRES replication. This mutation could possibly have a stimulatory effect either on RNA replication, or the viral structural proteins translation, or viral particle formation, or replicative complexes compartmentalization, etc. However, the most expected effect was an increase in viral RNA synthesis. Therefore, BHK-21 cells were transfected with in vitro-synthesized genomes of different VEEV variants, metabolically labeled the newly synthesized viral RNAs with [$^3$H]uridine in the presence of ActD for 4 h beginning 4.5 h post electroporation, and the RNA was analyzed by electrophoresis in agarose gels (FIG. 4A).

As expected, VEEV/IRES was capable of subgenomic RNA synthesis, which indicated that the IRES introduced at the 3' end of the subgenomic RNA 5'UTR did not interfere with the subgenomic promoter activity. VEEV/mutSG/IRES and its variants with adaptive mutations in nsP2 produced no detectable SG RNAs. Thus, 13 mutations introduced into the promoter sequence of these genomes completely abolished the transcription of the subgenomic RNA. Surprisingly, the adaptive mutations in the nsP2 did not have a noticeable effect on RNA genome replication, and VEEV/mutSG/IRES/1 and VEEV/mutSG/IRES/2 genome RNAs replicated as efficiently as did the originally designed VEEV/mutSG/IRES genome. Moreover, the genome RNA replication of all of the variants was very similar to that of VEEV TC-83. No effect of these mutations was detected in the context of the original VEEV TC-83 RNA as well (see lanes corresponding to VEEV/1 and VEEV/2). This finding strongly suggested that adaptation did not result in an increase in RNA replication.

Figures 4A, 4B:
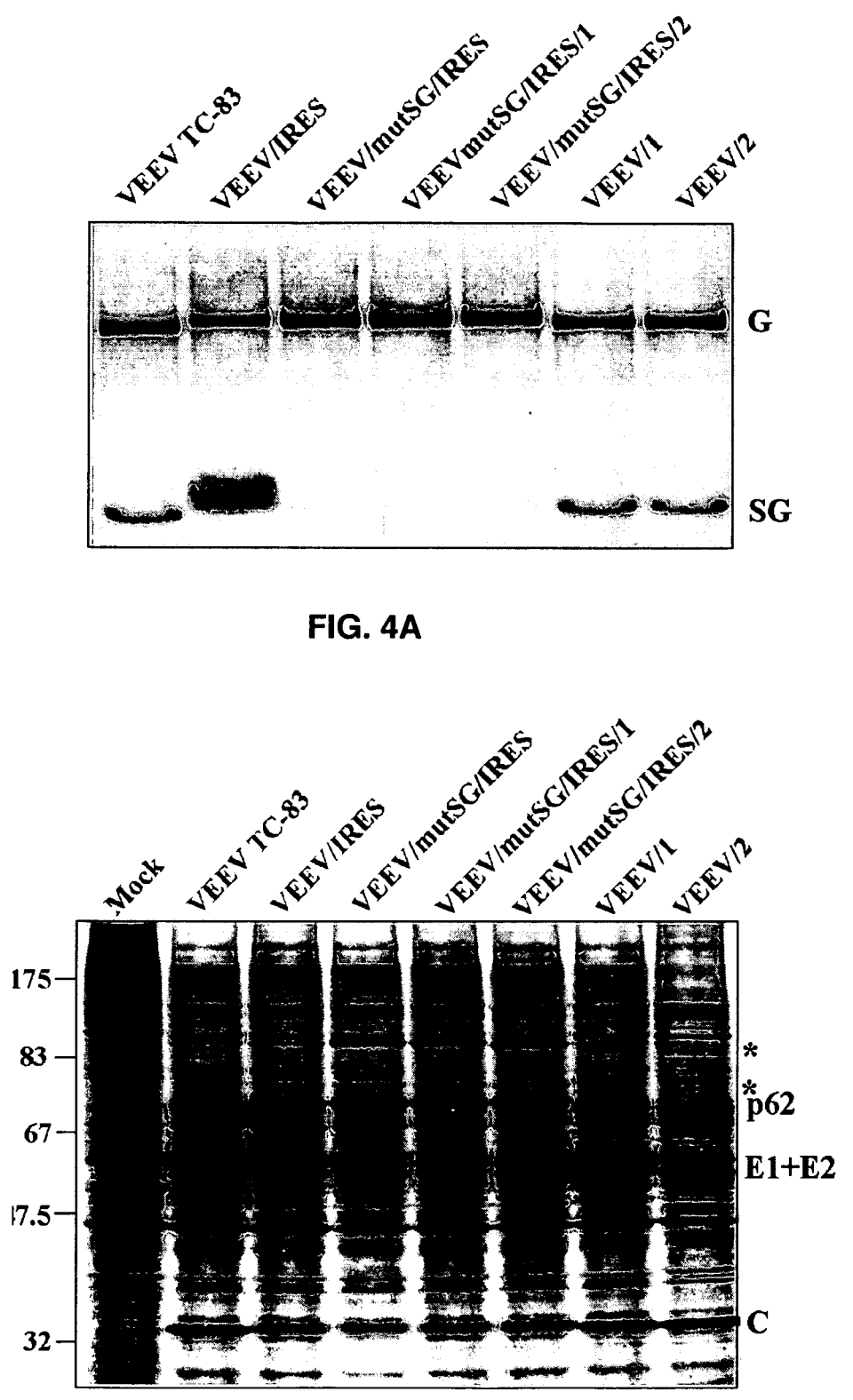

Synthesis of viral structural proteins was evaluated at 12 h post electroporation (FIG. 4B). By that time, VEEV/IRES- and VEEV/mutSG/IRES-specific capsid and likely other structural proteins were synthesized ~2-fold less efficiently than in the cells transfected with VEEV TC-83 RNA. This reasonably small difference does not explain the more than 4 and 7 orders of magnitude lower infectious titers of VEEV/IRES and VEEV/mutSG/IRES viruses, respectively (compared to the titers of VEEV TC-83), detected in samples harvested at 12 h post transfection. Moreover, no difference between the synthesis of viral proteins in BHK-21 cells containing the original VEEV/mutSG/IRES genomes versus VEEV/mutSG/IRES/1 and VEEV/mutSG/IRES/2 with adaptive mutations in the nsP2 was detected in this and other experiments. The distinguishing feature of the patterns of the labeled proteins in the cells infected with the IRES-containing viruses was in the presence of two additional bands, which were identified by mass spectrometry as heat-shock proteins Hsp90 and Hsp72. The biological significance of their induction is not clear yet, but might result from some abnormalities in viral structural protein(s) folding leading to stress development in the cells with the structural proteins expressed from the IRES.

In additional experiments, the intracellular distribution of the viral glycoproteins in cells infected with VEEV TC-83, VEEV/mutSG/IRES and VEEV/mutSG/IRES/1 were assessed and the presence of these proteins on the cell surface was analyzed by staining with VEEV-specific antibodies. No noticeable difference in the distribution of the glycoproteins was identified. The possibility that the adaptive mutations caused the formation of an additional packaging signal in the viral genome was examined; the mutation-containing fragment (corresponding to nt 2533-2950 of the VEEV genome) was cloned into the 3' UTR of VEEV/mutSG/IRES genome, and the recombinant in vitro-synthesized RNA was tested in the infectious center assay. No increase in plaque size or virus titers, compared to those of the original VEEV/mutSG/IRES, was detected.

In another variant, a subgenomic promoter and a VEEV capsid-coding sequence was cloned into the 3'UTR of VEEV/mutSG/IRES genome to test whether the additional capsid expression from the subgenomic RNA would increase the efficiency of virus replication. This modification also did not have any positive effect on virus titers. Last, whether VEEV/mutSG/IRES produced genome-free subviral particles instead of infectious virus was analyzed. It was observed that this was not the case: cells transfected with VEEV/mutSG/IRES RNA and metabolically labeled with [$^{35}$S]methionine did not produce subviral particles that could be detected by ultracentrifugation in sucrose gradients (data not shown). Thus, taken together, the above-described complex analysis did not point to obvious mechanistic explanations for the very inefficient replication of the original VEEV/mutSG/IRES or for the positive effect of the detected mutations in VEEV nsP2 on the replication of the IRES-containing virus. However, an aim of the present invention was the development of the VEEV variants, whose replication depends on the EMCV IRES function, and both VEEV/IRES and VEEV/mutSG/IRES/1 meets this goal.

Example 15

Replication of the IRES-Dependent VEEV Variants in the Mosquito Cells and Mosquitoes The accumulated data about alphavirus replication unambiguously demonstrate their genetic instability and high rate of evolution, resulting in the deletion of any heterologous genes (17, 40), particularly if they have a negative effect on virus replication. Therefore, whether the designed EMCV IRES insertions would be stable and render the viruses incapable of replication in mosquito cells was examined. To test this, $C_7$10 mosquito cells were infected with VEEV/IRES and VEEV/mutSG/IRES viruses harvested at 24 h postelectroporation of the in vitro-synthesized RNAs into BHK-21 cells. VEEV/mutSG/IRES was used instead of the above-described VEEV/mutSG/IRES/1, with an adaptive mutation $Y_{370} \rightarrow C$ in the nsP2, to test the entire library of the variants, released after the RNA transfection, for the ability to establish replication in mosquito cells.

On the first passage, at 48 h post infection of $C_7$10 cells the titer of VEEV/IRES approached $1.5 \times 10^{10}$ PFU/ml, and a similar titer was detected in the stock, harvested after the second passage (FIGS. 5A and 5B). The titers of VEEV/mutSG/IRES, in contrast, were 150 PFU/ml after the first passage (this likely reflected residual virus used for infection rather than nascent virus produced in the mosquito cells), and below the detection limit after the following second passage (FIGS. 5A and 5B). In additional experiments, the plaque-purified variants of VEEV/mutSG/IRES that contained adaptive mutations in nsP2 were passaged in $C_7$10 cells. No infectious virus was ever recovered after two blind passages.

In another experiment, Ae. aegypti mosquitoes were intrathoracically inoculated with ca. $10^5$ PFU of VEEV TC-83 and the VEEV/mutSG/IRES/1 variant. None of the 17 mosquitoes inoculated with the IRES mutant replicated detectably in Ae. aegypti, whereas 17/17 mosquitoes inoculated with the TC-83 parent strain replicated to detectable levels in the CFE assay, with a mean titer of over $10^6$ PFU/mosquito. Thus, the IRES-containing VEEV variant VEEV/mutSG/IRES/1 was incapable of replicating in mosquito cells both in vitro and in vivo.

To explain the high titers of VEEV/IRES (capable of producing the subgenomic RNA variant) after passaging in mosquito cells, two individual plaques were randomly selected and the IRES-containing fragment of the genome was sequenced. In both isolates, the IRES sequence was no longer present in the viral genomes, as, and only 13 (SEQ ID NO: 4) and 15 (SEQ ID NO: 5) residual nucleotides of the original IRES were found (FIG. 5C). Thus, passaging of VEEV/IRES variant in mosquito cells led to an accumulation of the IRES-negative variants, and VEEV/mutSG/IRES (that lacked the subgenomic promoter) did not develop mutants capable of replicating efficiently in mosquito cells.

Example 16

VEEV/mutSG/IRES/1 Variant Demonstrates an Attenuated Phenotype

Figures 6, 7, 8:
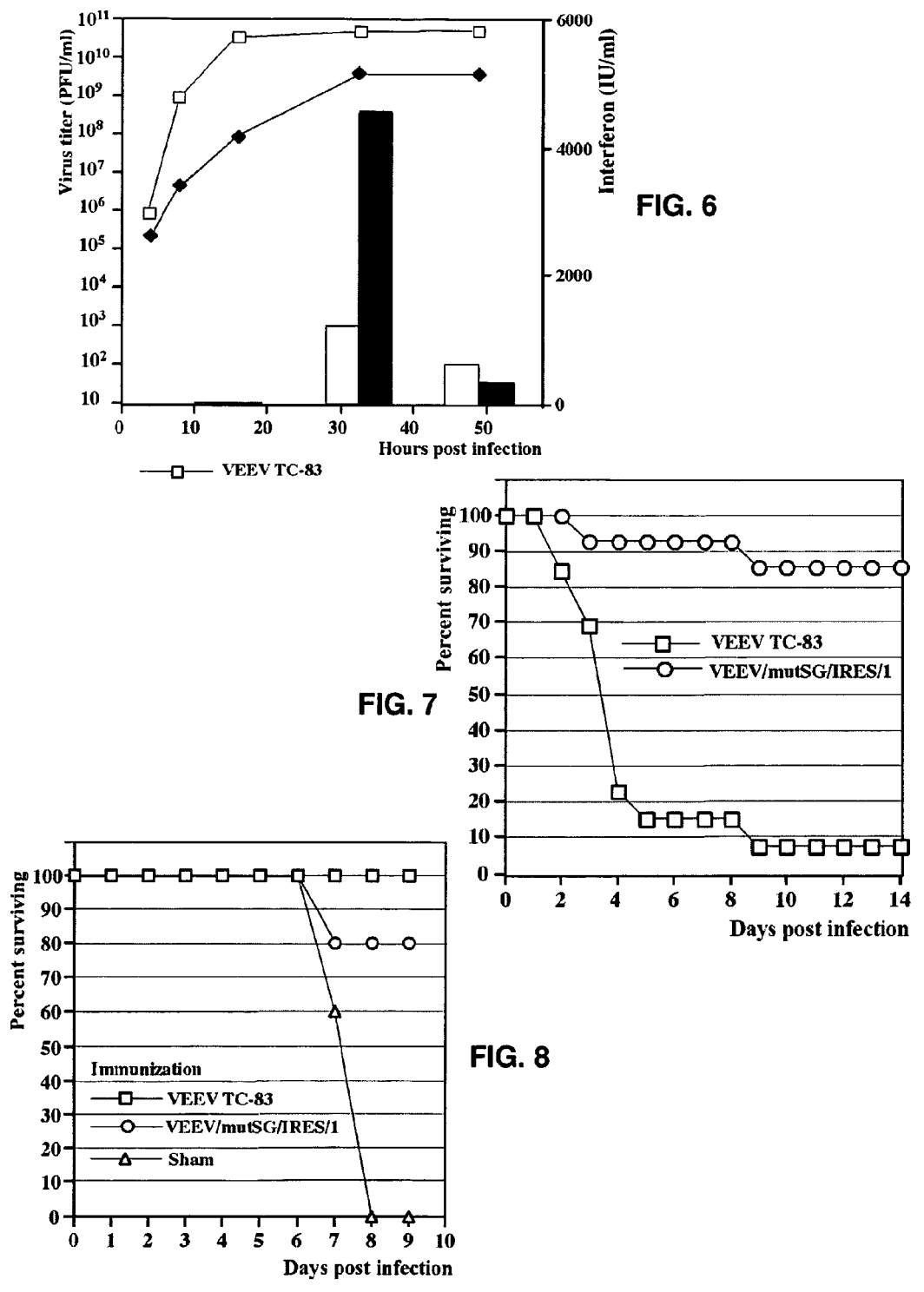

The present invention was aimed at development of VEEV variants incapable of replicating in cells of mosquito origin (and, correspondingly, in mosquito vectors) but demonstrating a more attenuated phenotype in vertebrates than the parental VEEV TC-83. The slower replication rates of VEEV/mutSG/IRES/1 variant raised a concern that this virus might be incapable of replicating in vertebrate cells with intact IFN-a/b production and signaling. However, this was not the case. FIG. 6 demonstrates that VEEV/mutSG/IRES/1 replicated in the NIH 3T3 cells, which have no defects in IFN-alpha/beta secretion and signaling, to the titers above $10^9$ PFU/ml. Its replication caused a more efficient IFN-a/b induction (FIG. 6), but apparently the IFN release did not abrogate the already established virus replication. As shown in BHK-21 cells (FIG. 2C), replication of VEEV/mutSG/IRES/1 was less efficient than that of the VEEV TC-83, suggesting that the IRES-dependent mutant might be attenuated in vivo. Indeed, after the i.c. inoculation of 6-day-old mice with ca. $10^6$ PFU. 86% survived the infection and did not develop signs of encephalitis; in contrast, 92% of mice were killed by the same dose of VEEV strain TC-83. Taken together, these data indicate that genetically modified, IRES-dependent VEEV was more attenuated than the parental VEEV TC-83.

Nevertheless, the VEEV/mutSG/IRES/1 variant remained immunogenic in both neonatal and adult mice. Of the twelve 6-day-old mice that survived i.c. inoculation with VEEV/mutSG/IRES/1, 10 survived s.c. challenge with $10^4$ PFU of wild-type VEEV strain 3908 administered 5 weeks later; in contrast, of 12 sham (PBS)-infected mice challenged in the same manner, none survived (FIG. 7). The VEEV/mutSG/IRES/1 was also immunogenic in adult mice; one s.c. immunization with ca. $10^6$ PFU protected 80% of mice against s.c. challenge 3 weeks later with $10^4$ PFU (~$10^4$ $LD_{50}$) of VEEV strain 3908 (FIG. 8). Neutralizing antibody titers ($PRNT_{80}$) were undetectable <1:20 in all of these mice immediately before challenge, suggesting that the incomplete protection after 1 vaccination was likely a result of lower level of IRES-containing virus replication in vivo. Thus, its high level of attenuation confers a high degree of safety, but repeated vaccinations will be likely required.

Example 17

Figure 9:
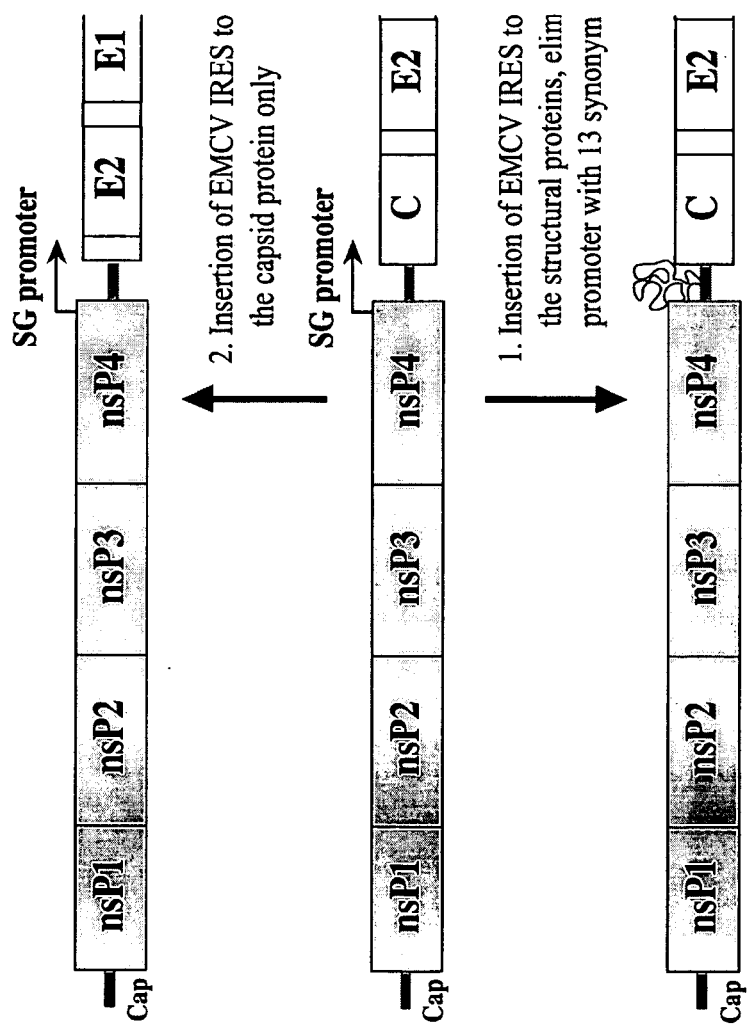
FIG. 9 shows a schematic method of generating attenuated, recombinant alphavirus incapable of infecting mosquitoes.

Expression Strategy to Reduce Attenuation but Maintain Lack of Mosquito Infectivity In a separate embodiment of the present invention, a novel expression strategy was designed to reduce attenuation but maintain lack of mosquito infectivity. This strategy involved placing the IRES downstream of the envelope glycoprotein genes, with the capsid gene at the 3' end of the subgenomic region just upstream of the 3' UTR. (FIG. 9). Thus, a subgenomic message was made, with the envelope protein genes translated in a cap-dependent manner but the capsid protein translated in an IRES-dependent manner. Replication of this new IRES mutant in BHK and Vero cells was again efficient, but could not be detected in C7/10 mosquito cells. Intrathoracic inoculation of 20 *Aedes aegypti* adult female mosquitoes yielded no evidence of replication. When this IRES version 2 was used to vaccinate mice, all 10 seroconverted with mean titers about 2-fold lower than induced by normal TC-83, and all 10 mice were protected by IRES version 2 from lethal, subcutaneous challenge. Therefore, the new IRES expression strategy appears to result in less attenuation while retaining the mosquito-incompetent phenotype.

TABLE 1

Immunogenicity and efficacy of TC-83 IRES mutants

| Vaccine strain | Fraction seroconverted | Mean neutralizing Ab titer ± SD | Fraction protected against lethal VEEV challenge |
|---|---|---|---|
| IRES version 1 | 0/10 | <20 | 8/10 |
| IRES version 2 | 10/10 | 224 ± 260 | 10/10 |
| TC-83 | 5/5 | 576 ± 143 | 5/5 |
| Sham | 0/5 | <20 | 0/5 |

Example 18

Recombinant Chikungunya Based Viruses

Figure 10:
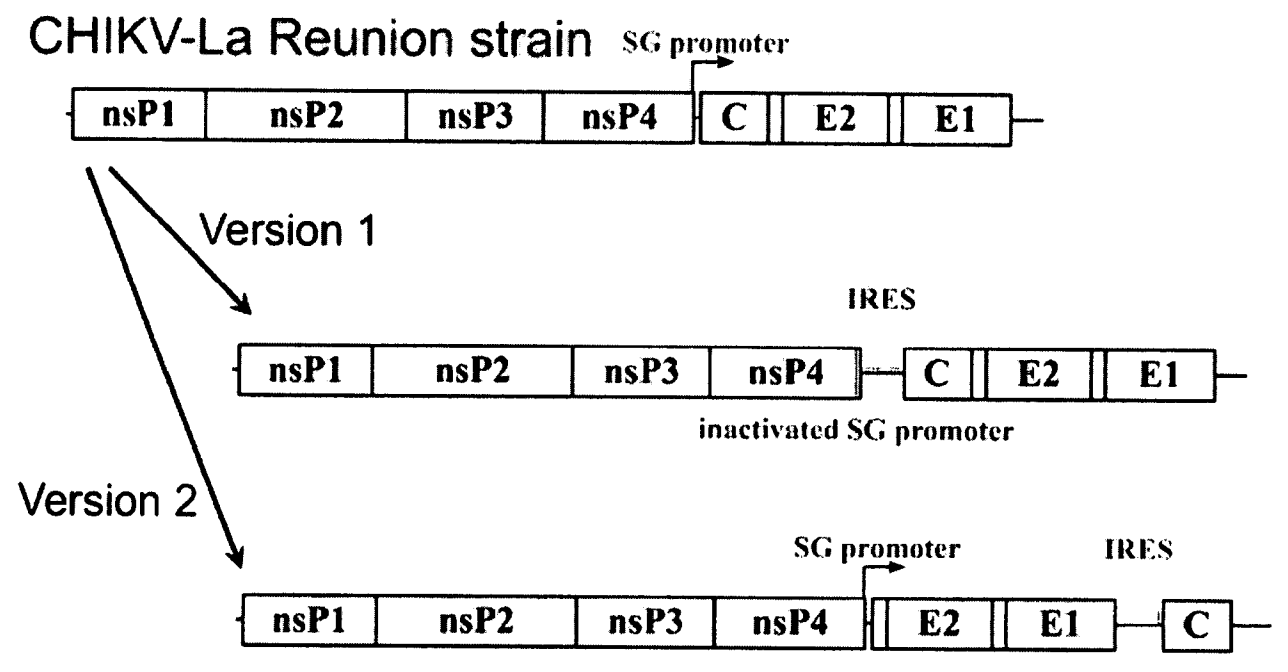

Based on the attenuation strategy described supra, two (2) chikungunya virus mutants were designed, that employed the encephalomyocarditis virus (EMCV) internal robosome entry site to alter gene expression. The first version CHIKV/IRESv1 (FIG. 10) contained 13 synonymous mutations to eliminate activity of the subgenomic promoter, and the addition of the IRES in the intergenic region upstream of the structural protein open reading frame (ORF). The second version CHIKV/IRESv2 (FIG. 10) retained the subgenomic promoter but positioned the capsid protein gene downstream of the envelope protein genes and behind the IRES.

Figure 11:
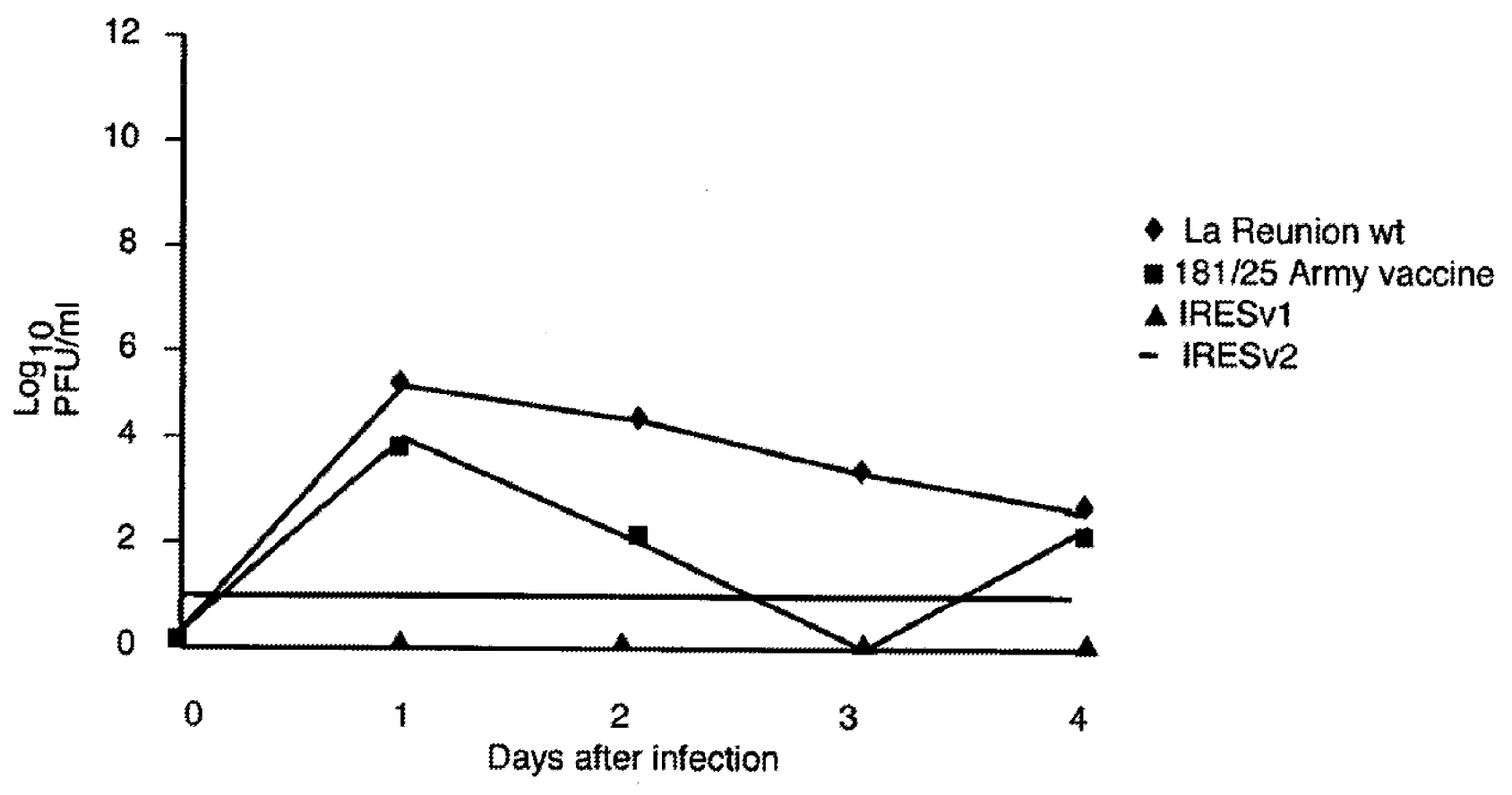
Figure 12:
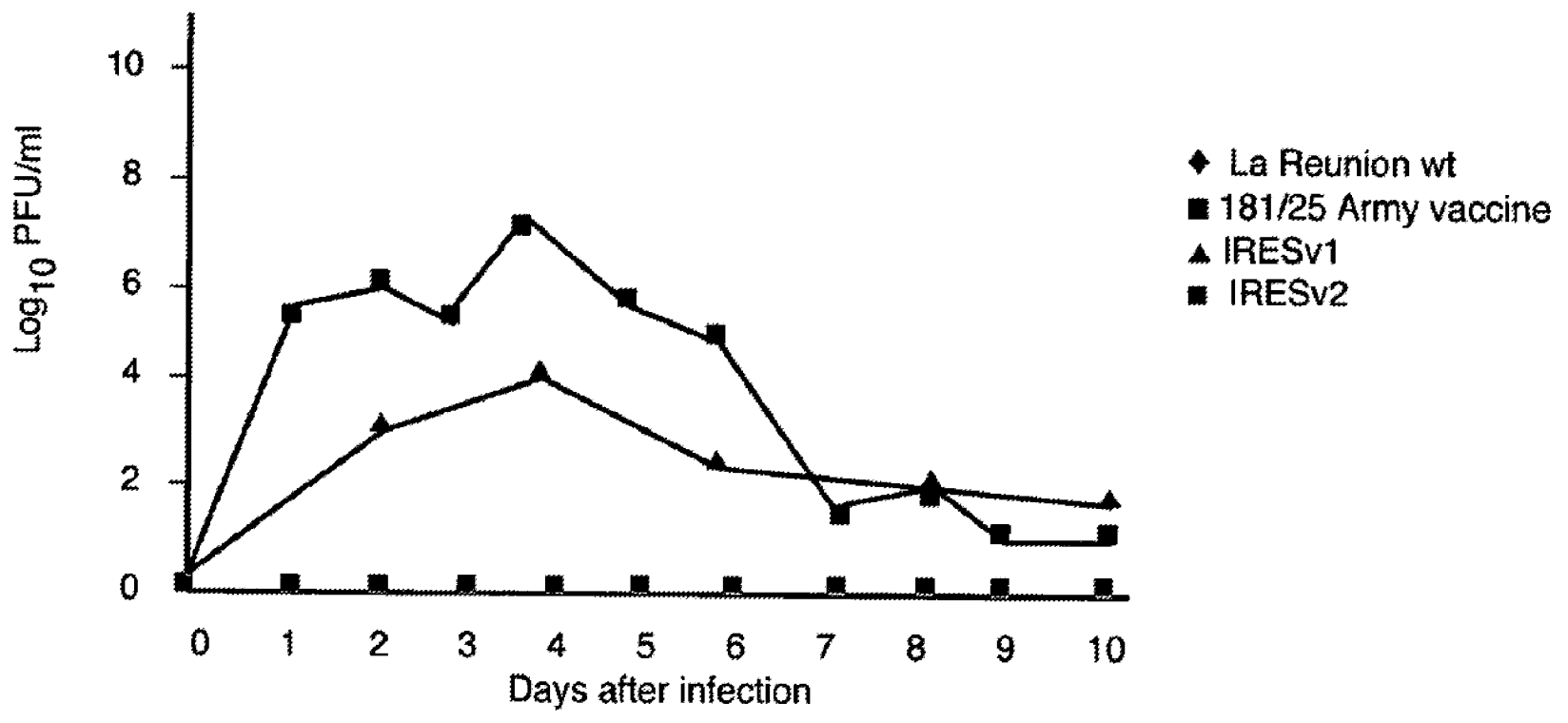
Figure 13:
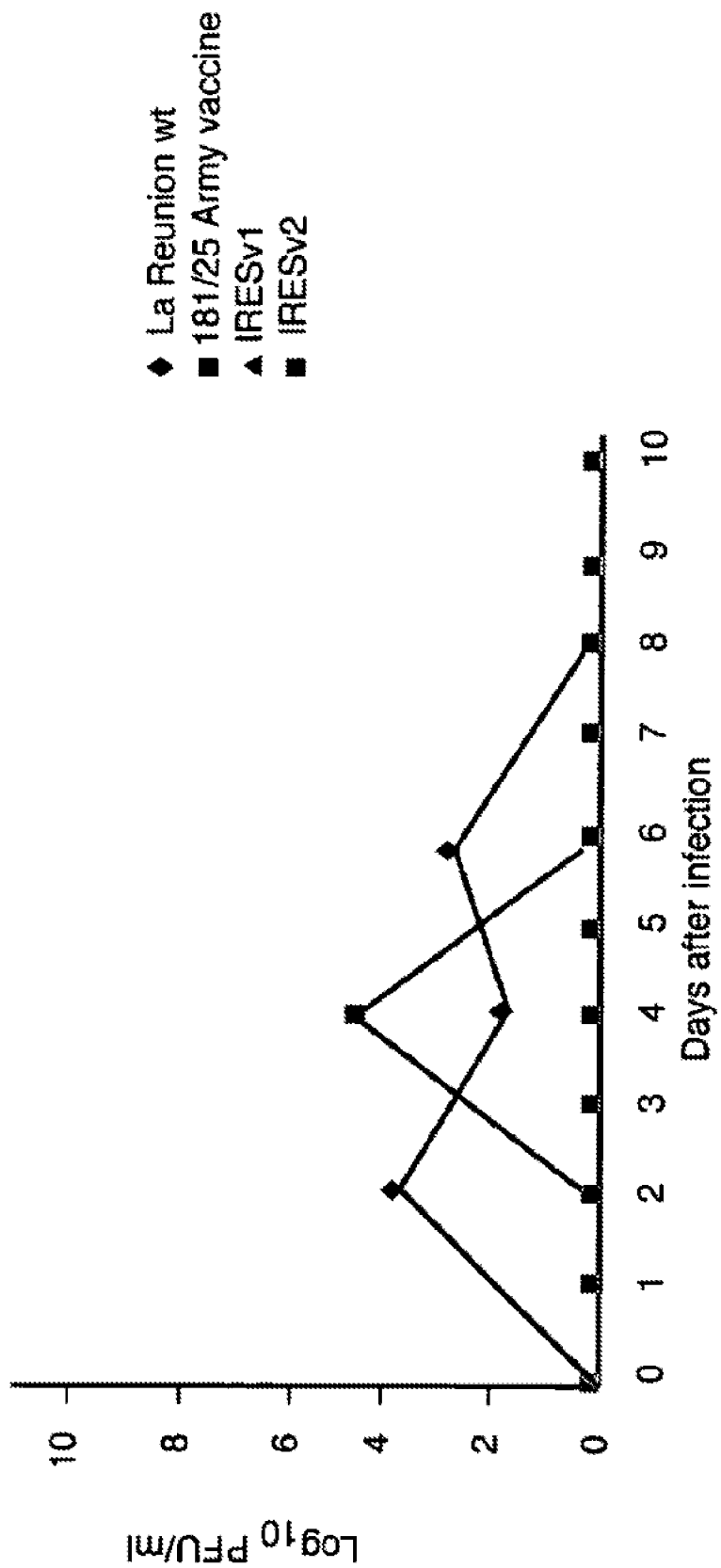
FIG. 13 shows virus titers in the brains of 6-day-old CD1 mice after subcutaneous infection with CHIKV strains ($10^6$ PFU). Dashed line is the limit of detection in the plaque assays.

Viruses rescued from these constructs were tested for attenuation in the baby CD1 mouse model (46) and compared to the parent La Reunion (LR) CHIKV strain as well as a vaccine strain developed by the U.S. Army (45) 181/25 that was highly immunogenic in human volunteers but showed some reactivity (44). The results demonstrated that both IRES mutants produced less viremia (FIG. 11) and less replication in the legs (FIG. 12) or brains (FIG. 13) of 6-day-old mice compared for the LR or 181/25 strains.

Example 19

Vaccinated with CHIKV/IRESv1 and CHIKV/IRESv2

Figure 14:
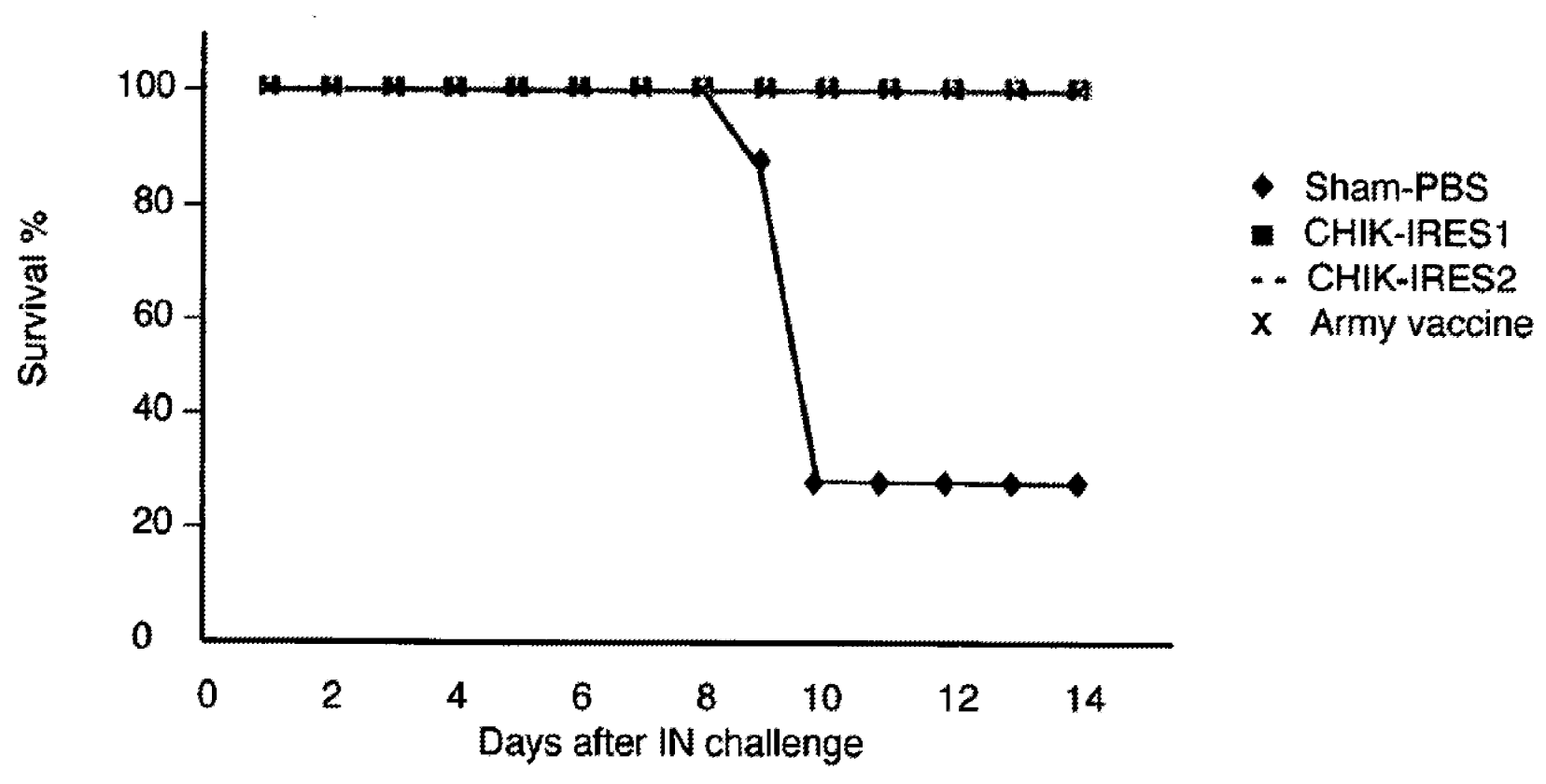

Adult CD1 mice were vaccinated with the CHIKV/IRES versions 1 or 2 described supra, and compared with 181/25 for their ability to protect from intranasal challenge 4 weeks later with the Ross CHIKV strain. All 3 vaccine strains provided complete protection, which was significantly better than sham vaccination (FIG. 14). Neutralizing antibody titers were similar for cohorts immunized with CHIK/IRESv1 and v2, as well as 181/25 (Table 2). These results indicate that the IRES attenuation approach for CHIK produces better attenuation and equivalent immunogenicity and protection compared to the U.S. Army 181/25 strain.

TABLE 2

Seroconversion of Outbred Mice After Vaccination

| Mouse Number | PRNT$_{80}$ titer | | |
|---|---|---|---|
| | CHIKV-IRESv1 | CHIKV-IRESv2 | 181/25 |
| 1 | 80 | 40 | 80 |
| 2 | 40 | 80 | 80 |
| 3 | 40 | 80 | 80 |
| 4 | 80 | 160 | 80 |
| 5 | 40 | 40 | 40 |
| 6 | 160 | 80 | 80 |
| 7 | 20 | 80 | 40 |
| 8 | 20 | 40 | 40 |
| 9 | 80 | 80 | 80 |
| 10 | | 80 | |
| % Seroconversion | 100 | 100 | 100 |
| Mean titer | 62 | 76 | 67 |
| STD | 44 | 35 | 20 |

Vaccination with $10^5$ PFU, single dose

Example 20

Evaluation of the Ability of CHIK/IRESv1 Virus to Infect C6/36 Mosquito Cells

CHIK/IRESv1 was also tested for its ability to infect C6/36 mosquito cells or Ae. aegypti mosquitoes to determine environmental safety. After 5 blind, serial passages in mosquito cells with inoculum titers of ca. 105 Vero cell plaque forming units, no evidence of viral replication was detected by cytopathic effect assays or RT-PCR; A positive control of the LR CHIKV strain replicated as expected. Cohorts of 20 Ae. aegypti were also inoculated intrathoracically with ca 104 Vero cell plaque forming units, no infection was detected by cytopathic effect assays or RT-PCR for CHIK/IRESv1, while the LR strain replicated in all 20 inoculated mosquitoes. These results indicate that the CHIK/IRESv1 is incapable of replicating in mosquitoes or mosquito cells.

The following references were cited herein:
1. Aguilar, P. V. et al., 2007, *J Virol* 81:3866-76.
2. Alevizatos, A. C. et al., 1967, *Am J Trop Med Hyg* 16:762-8.
3. Barton, D. J. et al., 1999, *J Virol* 73:10104-12.
4. Berge, T. O. et al., 1961, *Am. J. Hyg.* 73:209-218.
5. Blaney, J. E., Jr. et al., 2006, *Viral Immunol* 19:10-32.
6. Blaney, J. E., Jr. et al., 2005, *J Virol* 79:5516-28.
7. Bredenbeek, P. J. et al., 1993, *J. Virol.* 67:6439-6446.
8. Burke, D. S. et al., 1977, *J Infect Dis* 136:354-9.
9. Dal Canto, M. C., and S. G. Rabinowitz, 1981, *J Neurol Sci* 49:397-418.
10. Davis, N. L. et al., 1995, *Virology* 212:102-110.
11. Davis, N. L. et al. 1991, *Virology* 183:20-31.
12. Davis, N. L. et al., 1989, *Virology* 171:189-204.
13. Garmashova, N. et al., 2007. *J Virol* 81:13552-65
14. Garmashova, N. et al. 2006, *J Virol* 80:5686-96.
15. Garmashova, N. et al., 2007, *J Virol* 81:2472-84.
16. Gorchakov, R. et al., 2004, *J Virol* 78:61-75.
17. Gorchakov, R. et al., 2007, *Virology* 366:212-25.
18. Griffin, D. 2001. Alphaviruses, p. 917-962. In Knipe and Howley (ed.), Fields' Virology, Fourth Edition. Lippincott, Williams and Wilkins, NY.
19. Hart, M. K. et al., 2000, Vaccine 18:3067-75.
20. Jan, E., and P. Sarnow. 2002. *J Mol Biol* 324:889-902.
21. Johnson, K. and D. Martin. 1974. *Adv. Vet. Sci. Comp. Med.* 18:79-116.
22. Khromykh, A. A. et al., 2001, *J Virol* 75:4633-40.
23. Kinney, R. M. et al. 1993, *J. Virol.* 67:1269-1277.
24. Kinney, R. M. et al., 1989, *Virology* 170:19-30.
25. Kuhn, R. J. et al., 1996, *J Virol* 70:7900-9.
26. Lemm, J. A. et al., 1990, *J. Virol.* 64:3001-3011.
27. Liljeström, P. et al., 1991, *J. Virol.* 65:4107-4113.
28. Morrill, J. C. et al., 1991, *Vaccine* 9:35-41.
29. Murphy, et al. 2001. Immunization against viral diseases, p. 435-467. In D. Knipe and Howley (ed.), Fields' Virology, 4th Ed. Lippincott, Williams and Wilkins, New York.
30. Nugent, C. I. et al., 1999, *J Virol* 73:427-35.
31. Paessler, S. et al., 2003, *J Virol* 77:9278-86.
32. Pedersen, C. E. et al., 1972, *Am J Epidemiol* 95:490-6.
33. Petrakova, O. et al., 2005, *J Virol* 79:7597-608.
34. Pittman, P. R. et al., 1996, *Vaccine* 14:337-43.
35. Pugachev, K. V. et al., 2000, *J Virol* 74:10811-5.
36. Rice, C. M. et al., 1987, J. Virol. 61:3809-3819.
37. Rivas, F. et al., 1997, J Infect Dis 175:828-32.
38. Russo, A. T. et al., 2006, *Structure* 14:1449-58.
39. Strauss, J. H., and E. G. Strauss, 1994, *Microbiol. Rev.* 58:491-562.
40. Thomas, J. M. et al., 2003, J Virol 77:5598-606.
41. Trgovcich, J. et al., 1996. Virology 224:73-83.
42. Weaver, S. C. 1997. Vector Biology in Viral Pathogenesis, p. 329-352. In N. Nathanson (ed.), Viral Pathogenesis. Lippincott-Raven, New York.
43. White, L. J. et al., 2001, J Virol 75:3706-18.
44. Edelman, R. et al. (2000). Am J Trop Med Hyg 62(6), 681-5.
45. Levitt, N. H. et al. (1986). Vaccine 4(3), 157-62.
46. Ziegler, S. A. et al. (2008). Am J Trop Med Hyg 79(1), 133-9.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

What is claimed is:

1. A live, attenuated Chikungunya (CHIK) virus comprising: a CHIK virus polynucleotide having (i) an inactivated subgenomic promoter, and (ii) an insertion of an encephalomyelocarditis virus internal ribosomal entry site (EMCV IRES) functional only in cells of vertebrate origin, between one end of nonstructural protein 4 (nsP4) coding sequence and initiating AUG of a subgenomic RNA coding sequence of the CHIK virus, wherein the subgenomic promoter is inactivated by clustered point mutations and wherein the CHIK virus is attenuated.

2. The live, attenuated CHIK virus of claim 1, wherein the subgenomic promoter is inactivated by clustered point mutations and the clustered point mutations are located in the 5' UTR of the subgenomic RNA.

3. The live, attenuated CHIK virus of claim 1, wherein the mutation of the subgenomic promoter does not modify the amino acid sequence of the carboxy terminus of non-structural protein 4.

4. A pharmaceutical composition comprising the live, attenuated, Chikungunya (CHIK) virus of claim 1 and a pharmaceutically acceptable carrier.

5. A method for inducing an anti-Chikungunya (CHIK) virus immune response in a subject, comprising administering to the subject the composition of claim 4.

6. The method of claim 5, wherein the subject is a human, a horse or other domestic animal.

7. An expression vector comprising a polynucleotide encoding the live, attenuated Chikungunya (CHIK) virus of claim 1.

8. An isolated host cell comprising the expression vector of claim 7.

9. The live, attenuated CHIK virus of claim 2, wherein the clustered point mutations comprise synonymous mutations at position 11, 12, 14, 17, 20, 22, 24, 25, 26, 27, 28, 29 and 30 of SEQ ID NO:1.

* * * * *

SEQUENCE LISTING

<160> NUMBER OF SEQ ID NOS: 6

<210> SEQ ID NO 1
<211> LENGTH: 38
<212> TYPE: RNA

```
<213> ORGANISM: Artificial Sequence
<220> FEATURE:
<223> OTHER INFORMATION: Synthetic oligonucleotide

<400> SEQUENCE: 1
ccccuauaac ucucuacggc uaaccugaau ggacuacg                    38

<210> SEQ ID NO 2
<211> LENGTH: 38
<212> TYPE: RNA
<213> ORGANISM: Artificial Sequence
<220> FEATURE:
<223> OTHER INFORMATION: Synthetic oligonucleotide

<400> SEQUENCE: 2
ccccgauuac guuguaugga ugauaaucua gaaacguu                    38

<210> SEQ ID NO 3
<211> LENGTH: 6
<212> TYPE: PRT
<213> ORGANISM: Artificial Sequence
<220> FEATURE:
<223> OTHER INFORMATION: synthetic peptide

<400> SEQUENCE: 3

Pro Ile Thr Leu Tyr Gly
1               5

<210> SEQ ID NO 4
<211> LENGTH: 44
<212> TYPE: DNA
<213> ORGANISM: Artificial Sequence
<220> FEATURE:
<223> OTHER INFORMATION: synthetic oligonucleotide

<400> SEQUENCE: 4
atggactacg acatagtcta gtccgccata tggccacaac catg             44

<210> SEQ ID NO 5
<211> LENGTH: 48
<212> TYPE: DNA
<213> ORGANISM: Artificial Sequence
<220> FEATURE:
<223> OTHER INFORMATION: synthetic oligonucleotide

<400> SEQUENCE: 5
atggactacg acatagtcta gtccgccaag tctatggcca caaccatg         48

<210> SEQ ID NO 6
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 6
atggactacg acatagtcta gtccgccaag atg                         33
```